(12) United States Patent
Porreca, Jr.

(10) Patent No.: US 9,283,151 B2
(45) Date of Patent: Mar. 15, 2016

(54) ENTERAL FEEDING TUBE HAVING UNCLOGGING LUMEN

(76) Inventor: Louis O. Porreca, Jr., Marlton, NJ (US)

( * ) Notice: Subject to any disclaimer, the term of this patent is extended or adjusted under 35 U.S.C. 154(b) by 631 days.

(21) Appl. No.: 12/605,316

(22) Filed: Oct. 23, 2009

(65) Prior Publication Data
US 2011/0098660 A1    Apr. 28, 2011

(51) Int. Cl.
*A61J 15/00* (2006.01)
*A61M 25/00* (2006.01)

(52) U.S. Cl.
CPC .......... *A61J 15/0003* (2013.01); *A61J 15/0015* (2013.01); *A61J 15/0069* (2013.01); *A61J 15/0073* (2013.01); *A61M 25/0026* (2013.01); *A61J 15/0049* (2013.01); *A61M 2025/0019* (2013.01)

(58) Field of Classification Search
CPC .......... A61M 1/0037; A61M 5/14228; A61M 2025/0019; A61M 25/0026; A61M 27/00; A61J 15/0003; A61J 15/0015; A61J 15/0049; A61J 15/0069; A61J 15/0073
USPC ................. 604/246, 266, 267, 514, 516, 910, 604/97.02, 98.02
See application file for complete search history.

(56) References Cited

U.S. PATENT DOCUMENTS

| 2,845,930 | A | * | 8/1958 | William | 600/560 |
| 3,211,151 | A | * | 10/1965 | Foderick et al. | 604/97.02 |
| 4,301,797 | A | * | 11/1981 | Pollack | 604/6.16 |
| 4,594,074 | A |   | 6/1986 | Andersen et al. | |

(Continued)

FOREIGN PATENT DOCUMENTS

| JP | 55-152215 A | 11/1980 |
| WO | WO 92/12756 A1 | 6/1992 |

(Continued)

OTHER PUBLICATIONS

Kimberly-Clark, MIC Transgastric-Jejunal Feeding Tube Instructions, 2 pages, 2003.

(Continued)

*Primary Examiner* — Bhisma Mehta
*Assistant Examiner* — Larry R Wilson
(74) *Attorney, Agent, or Firm* — Flaster/Greenberg P.C.

(57) ABSTRACT

An enteral feeding device and methods of using such device to unclog a feeding tube are described herein, wherein the device includes a first tube having a distal end and a proximal end. The first tube defines a feeding lumen that extends longitudinally through at least a portion of the first tube. The first tube has at least one distal opening capable of allowing introduction of nutrients and/or medicaments from within the feeding lumen through the opening into a gastrointestinal area of a patient when the enteral feeding tube is implanted in a patient. The device also has a wall having a distal end and a proximal end, which extends longitudinally within at least a portion of the first tube. The wall has an exterior surface and an interior surface. At least a portion of the exterior surface of the wall contacts the feeding lumen. The interior surface of the wall and/or the first tube define an inflatable lumen having a proximal end and a distal end, wherein the inflatable lumen extends longitudinally through at least a portion of the feeding lumen, and wherein the wall is capable of changing a volume of the feeding lumen by allowing for deflation of the inflatable lumen through removal of a fluid from the inflatable lumen and/or inflation of the inflatable lumen through introduction of a fluid into the inflatable lumen.

29 Claims, 6 Drawing Sheets

(56) References Cited

U.S. PATENT DOCUMENTS

| | | | |
|---|---|---|---|
| 4,637,814 A | | 1/1987 | Leiboff |
| 4,781,678 A | * | 11/1988 | de Couet ............. A61M 1/0037 604/266 |
| 4,894,056 A | | 1/1990 | Bommarito |
| 5,221,256 A | * | 6/1993 | Mahurkar ....................... 604/43 |
| 5,527,280 A | | 6/1996 | Goelz |
| 5,718,678 A | * | 2/1998 | Fleming, III .................... 604/43 |
| 6,283,719 B1 | | 9/2001 | Frantz et al. |
| 6,511,474 B1 | | 1/2003 | Andersen |
| 6,827,710 B1 | * | 12/2004 | Mooney et al. ............... 604/500 |
| 7,041,083 B2 | | 5/2006 | Chu et al. |
| 7,048,722 B2 | * | 5/2006 | Quinn ........................... 604/270 |
| 7,066,917 B2 | | 6/2006 | Talamonti |
| 2002/0198502 A1 | | 12/2002 | Vohsing |
| 2004/0059277 A1 | * | 3/2004 | Maguire et al. .............. 604/6.16 |
| 2008/0097350 A1 | * | 4/2008 | Bell et al. ...................... 604/266 |

FOREIGN PATENT DOCUMENTS

| | | |
|---|---|---|
| WO | WO 95/04564 A1 | 2/1995 |
| WO | WO 00/26537 A1 | 11/2000 |

OTHER PUBLICATIONS

Bionix Medical Technologies Brochure, "Remove the Clog. Not the Tube." 1 page 2008.

ALS Association, "FYI . . . Information About Feeding Tubes," 6 pages 1996.

Corflo® Enteral Feeding Tubes, www.viasyshealthcare.com/prod_serv/prodDetail.aspx?config=ps_prodDtl&prodID . . . , 1 page, 2008.

Enteral Access Catheters & Accessories, www.kca.com.au/heatlhcare/enteral.htm, 4 pages, 2008.

P. Guenter, "Administering Medications Via Feeding Tubes: What Consultant Pharmacists Need to Know," Consultant Pharmacist, Jan. 1999, 7 pages.

"A Close-Up of the Clog Zapper," http://rn.modernmedicine.com/rnweb/data/articlestandard/rnweb/032005/142656/rn_2devi . . . , 2008, 2 pages.

R. Smith et al., "2 Devices that Unclog Feeding Tubes," http:/rn.modernmedicine.com/rnweb/content/printContentPopup.jsp?id=142656, 7 pages, 2005.

* cited by examiner

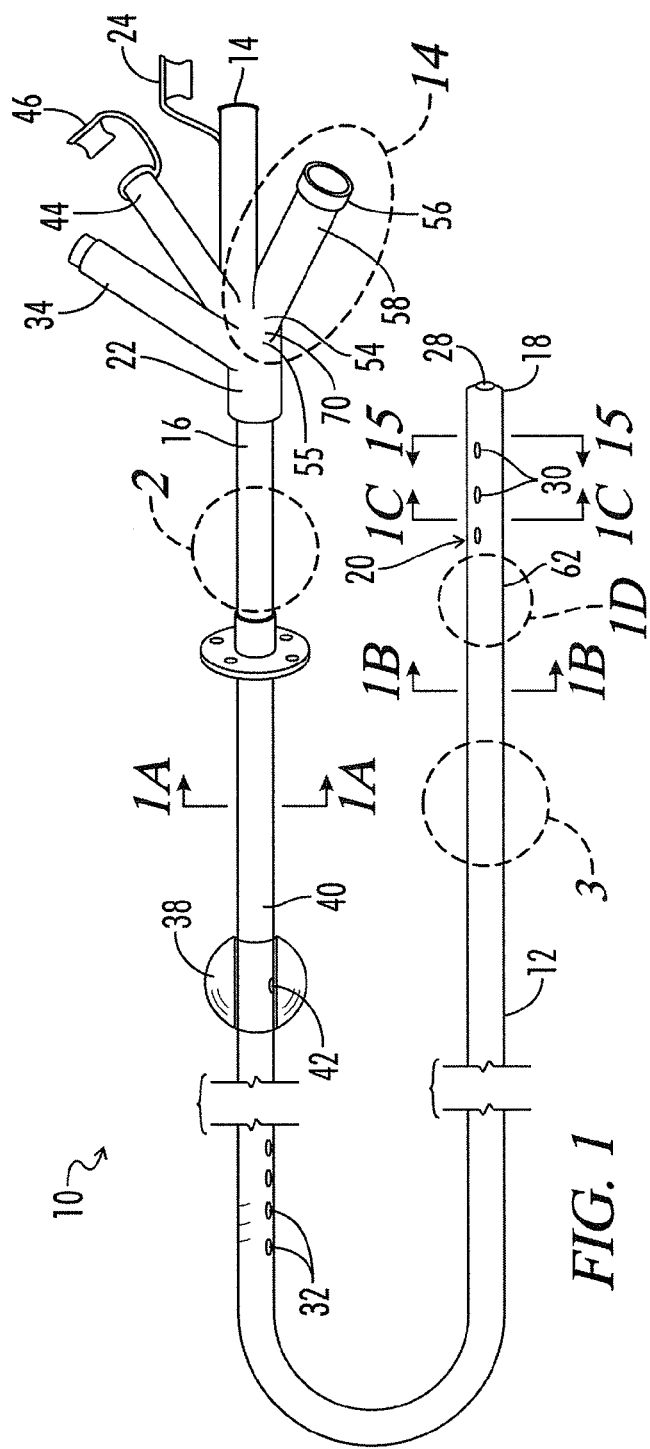
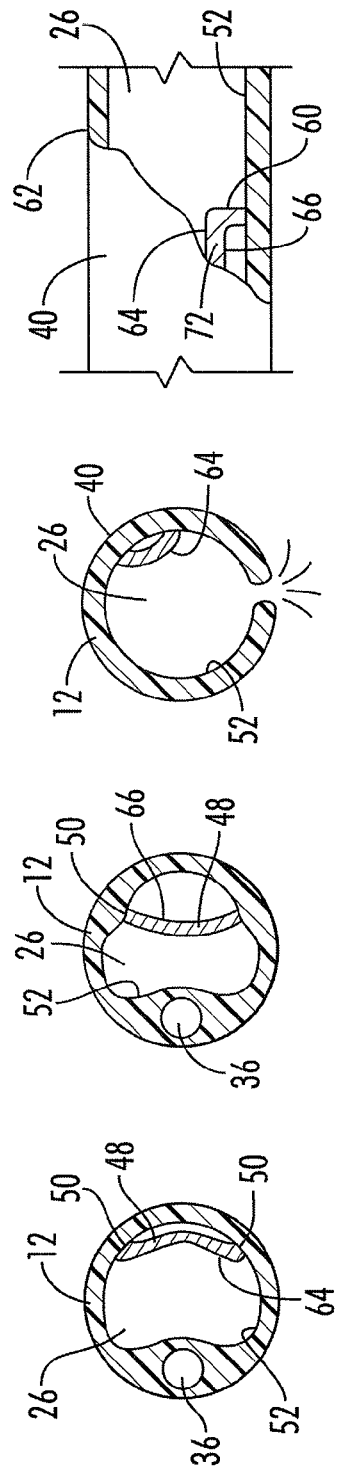
FIG. 1
FIG. 1A
FIG. 1B
FIG. 1C
FIG. 1D

ENTERAL FEEDING TUBE HAVING UNCLOGGING LUMEN

BACKGROUND OF THE INVENTION

1. Field of the Invention

The invention relates to the field of enteral feeding tubes such as gastrostomy tubes and jejunostomy tubes, and unclogging such tubes.

2. Description of Related Art

Many people who are too ill to feed themselves, for example, they are not able to eat, swallow food or medication, and the like (such as from cancer, neurological disorders, etc.) are typically fed through enteral feeding tubes. Enteral nutrition is a type of hyperalimentation and metabolic support in which nutrient formulas or medicaments can be delivered directly to the gastrointestinal tract, i.e., enteral feeding involves delivery of nutrients, etc., directly into the stomach, duodenum or jejunum. Long-term enteral feeding tubes can be gastrostomy tubes (G-tubes), jejunostomy tubes (J-tubes) and nasogastric tubes (NG-tubes). Such in-dwelling tubes work well, but have a tendency to clog.

In a gastrostomy tube, a feeding tract (or stoma) is created between the stomach and upper abdominal wall. Feeding is performed generally by administering food through a catheter or feeding tube inserted into the stoma, the distal end extending into the stomach and generally bolstered against the wall of the stomach. Gastrostomy tubes typically extend through the skin (i.e., percutaneously) into the stomach. Such tubes are generally surgically placed below the rib cage and slightly off to the left. G-tubes are easy to replace compared to other tubes and provide patient comfort and convenient care.

Jejunostomy tubes differ from G-tubes in that they are typically surgically implanted in the upper section of the small intestine (jejunum) just below the stomach. J-tubes are located lower and more towards the center of the abdomen than G-tubes. J-tubes are used when there is a need to bypass the stomach and to feed a patient directly into the intestinal tract. Such patients are generally fed with an enteral feeding pump. J-tubes may be secured by suturing.

Nasogastric tubes are used for patients who cannot ingest nutrients by mouth. The tube is placed in either nostril, passed down the pharynx through the esophagus and into the stomach, and is more usually associated with short-term feeding, unlike G- and J-tubes.

While all such tubes clog, more often, it is long-term enteral feeding tubes for critical care or long-term illness patients where clogging presents the greatest concern (i.e., in G-tubes and J-tubes). As such, tubes can be affected by the body, by backlog of nutrients or medicaments and the like, and the tubes themselves or the exit holes in the distal ends thereof can become blocked required unclogging and/or replacement of the tubes. Such clogging happens reasonably frequently and presents a significant challenge to long-term care. Generally, the first step in unclogging an enteral feeding tube is that if a nurse is present, he may flush the tube with fluids and/or other unclogging agents (such as water, ginger ale, powders and different dissolving agents, etc.) under pressure (such as through a syringe) to unclog the holes and/or the feeding tube. When this fails, the patient may have to have the tube replaced. Frequent tube replacement for long-term feeding tubes is expensive, can require visits to clinics or hospitals for long-term critical care patients in nursing homes, rehabilitation centers and convalescence centers. This can create a significant burden both financially and through use of resources (ambulances, EMT personnel, etc.). This process also is also a cause of great discomfort and presents danger to the patient each and every time feeding is cut off.

The prior art presents several potential solutions to the long-term enteral feeding tube clogging issue. U.S. Pat. No. 4,894,056 as well as a product known as the Introreducer™ are directed to small polycarbonate tubes that can be slipped down into an enteral feeding tube for forcing warm water or unclogging solution into the tube using the pressure distributor portion of the device.

International Patent Publication No. WO 92/12756 teaches a device for unclogging a J-tube. The device has a blunted end and a threaded portion. By rotating the handle of the device, it unclogs the tube by having the threaded portion dislodge and lift the clog from the tube. By twisting, it is hoped that there is reduced risk of perforation of the intestine from prior art plunging methods.

U.S. Patent Publication No. 2002/0198502 A1 teaches a clog preventing device in which a corrugated tube is placed (longitudinally slid) over a feeding tube attachment to prevent clogging as a result of kinking, compression or other effects of patient movement while sleeping.

Some feeding tubes are formed with special clog-resistant ends having a "bolus" on the distal end thereof. For example, U.S. Pat. No. 4,594,074 teaches use of an enteral feeding tube opening having a "bolus" on the end with a non-clogging opening that is elliptically shaped and slopes upward so as to prevent clogging in feeding through the tube.

U.S. Pat. No. 6,283,719 discloses an improvement for pumping through indwelling feeding tubes. The system is designed to make the pressure changes more noticeable so the automatic pumping device can work properly by differentiating a clogging event from other changes in pressure. When an actual clog is detected, the device goes into "clog clearing mode." The pump is said to be able to clear the clog without assistance of a nurse. The pump uses the feeding fluid in the system to unclog without the need to flush or use of other devices such as a flushing syringe or brush. The system remains in that mode until either the clog is removed or a preset period of time expires.

U.S. Pat. No. 7,041,083 teaches a low-profile percutaneous endoscopic gastrostomy tube in which there is a "tube-in-tube" configuration that allows for the primary gastrostomy tube to remain clean when feeding due to an inserted and removable tube. The primary tube extends from the stomach out of the device and folds over the main portion of the device.

U.S. Pat. No. 5,527,280 teaches a multilumen enteral feeding tube device in which there are three branches and three primary lumens. The main lumen is within a feeding tube that is a gastric tube having openings in tip to transmit feeding material or medicine to the stomach interior through one branch. Another branch of the device allows for introduction of a J-tube that runs through the center of the gastric tube coaxially allowing for introduction of materials to the intestines. A third lumen (fluid lumen) is defined within the wall of the gastric tube itself and is in communication with the further branch of the device for introducing fluid (air or water) to inflate or deflate a balloon using a syringe. The balloon is for securing the device in place when positioned in the patient.

While there have been attempts to unclog or prevent clogging of J- and G-tubes in patients on-site, such procedures have met with mixed results, and the primary technique still in use is flushing of the tube and/or replacement of the tube by the nurse or other health-care professional. Thus, there is still a need in the art for an improved device and/or method to easily unclog a J-tube, G-tube, NG-tube or other enteral feeding tube with the least disruption, inconvenience and discomfort to patients, thereby minimizing the need to visit a hospital or clinic for replacement of the tubes when standard unclogging procedures do not work.

BRIEF SUMMARY OF THE INVENTION

The invention provides a device and method for unclogging and/or preventing clogging of enteral feeding tubes, including NG-, J- and G-tubes in patients on-site, as an alternative to prior art routine flushing of the tube and/or replacement of the tube by the nurse or other health care professional. The device and/or methods described herein allow a health care professional to easily unclog a J-tube, G-tube, NG-tube or other enteral feeding tube with little disruption, inconvenience and discomfort to patients. It thus, minimizes the need to visit a hospital or clinic for replacement of the tubes.

The invention includes an enteral feeding device, comprising a first tube having a distal end and a proximal end, the first tube defining a feeding lumen that extends longitudinally through at least a portion of the first tube, the first tube having at least one distal opening capable of allowing introduction of nutrients and/or medicaments from within the feeding lumen through the opening into a gastrointestinal area of a patient when the enteral feeding tube is implanted in a patient; and a wall having a distal end and a proximal end, the wall extending longitudinally within at least a portion of the first tube, the wall having an exterior surface and an interior surface, wherein at least a portion of the exterior surface of the wall contacts the feeding lumen, wherein the interior surface of the wall and/or the first tube define an inflatable lumen having a proximal end and a distal end, wherein the inflatable lumen extends longitudinally through at least a portion of the feeding lumen, and wherein the wall is capable of allowing for deflation of the inflatable lumen through removal of a fluid from the inflatable lumen and/or inflation of the inflatable lumen through introduction of a fluid to effect a change of a volume of the feeding lumen.

In various embodiments herein, the enteral feeding device may have a first tube that is a single lumen feeding tube, may include a tube-within-a-tube configuration (i.e., it has at least a second tube extending longitudinally within the feeding lumen outside of the inflatable lumen along at least a portion of a length of the first tube), and/or may have at least two lumens defined by at least one septum (i.e., be configured as a multilumen tube) extending longitudinally along at least a portion of a length of the first tube, wherein at least one of the lumens within the first tube is the feeding lumen.

For multilumen configurations, the first tube may have two side-by-side D-shaped lumens, two lumens in a circle-C configuration, two coaxial lumens, three or more lumens, three lumens wherein two of the three lumens are side-by-side lumens that are arcuate wedge-shaped lumens and one of the three lumens has a semi-circular configuration, three coaxial lumens, three equally spaced arcuate lumens, where at least one of the three lumens is the feeding lumen, three lumens wherein two of the three lumens are side-by-side lumens and one of the three lumens has a circular cross section and is located either along an interior surface of the first tube or is defined by the septum between the two side-by-side lumens and other various configurations, provided that at least one of the lumens is the feeding lumen.

In various embodiments herein, the feeding lumen may extend along a full length of the first tube, and the distal end of the first tube may have a single opening (through an end thereof or along the sides of the first tube) or a plurality of distal openings, depending on a desired feeding tube configuration.

The first tube may be a gastrostomy tube, a jejunostomy tube, a nasogastric tube or other enteral feeding tube.

In other embodiments, the wall may comprise a flexible material and the enteral feeding device may further comprise a compressible bladder in communication with the proximal end of the inflatable lumen for removal of saline and/or air for deflation of the inflatable lumen and/or introduction of saline and/or air for inflation of the inflatable lumen. Alternatively, the device may further comprise a fitting being located on the device so that the interior space of the fitting is in fluid communication with the proximal end of the inflatable lumen and the fitting is capable of receiving an injected fluid therethrough for removing the fluid from the inflatable lumen for deflation thereof and/or introducing the fluid into the inflatable lumen for inflation thereof.

In one preferred embodiment herein, the interior surface of the wall defines the inflatable lumen. In another preferred embodiment, the interior surface of the wall together with an interior surface of the first tube defines the inflatable lumen. The inflatable lumen may extend from the distal end of the feeding lumen to the proximal end of the feeding lumen.

In a further embodiment, the enteral feeding device comprises a fluid within the inflatable lumen. In use, such fluid can be removed to change the volume of the feeding tube which change in volume creates a change in pressure in the feeding tube that affects a blockage in the tube.

The invention also includes an enteral feeding device, comprising a first tube having a distal end and a proximal end and having a length measured longitudinally therebetween, the first tube defining a feeding lumen that extends longitudinally through the first tube, the first tube having at least one distal opening capable of allowing introduction of nutrients and/or medicaments from within the feeding lumen through the opening into a gastrointestinal area of a patient when the enteral feeding tube is implanted in a patient; and a wall having a distal end and a proximal end and a length measured longitudinally therebetween, the wall extending longitudinally from the distal end of the first tube for at least a portion of the length of the first tube, the wall having an exterior surface and an interior surface, wherein at least a portion of the exterior surface of the wall contacts the feeding lumen, wherein the interior surface of the wall and/or the first tube define an inflatable lumen having a proximal end and a distal end, wherein the inflatable lumen extends along the length of the wall, and wherein the wall comprises a flexible material capable of allowing for deflation of the inflatable lumen through removal of a fluid from the inflatable lumen and/or inflation of the inflatable lumen through introduction of a fluid into the inflatable lumen to change a volume of the feeding lumen. In such a feeding device, the first tube may be at least one of a gastrostomy tube and a jejunostomy tube.

A method for unclogging an enteral feeding device when implanted in a patient is also described herein. In the method, the enteral feeding device comprises a first tube having a distal end and a proximal end and defining a feeding lumen that extends longitudinally through at least a portion of the first tube, wherein the first tube has at least one distal opening capable of allowing introduction of nutrients and/or medicaments from within the feeding lumen through the opening into a gastrointestinal area of a patient when the enteral feeding tube is implanted in a patient; and a wall having a distal end and a proximal end, the wall extending longitudinally within at least a portion of the first tube, and having an exterior surface and an interior surface, wherein at least a portion of the exterior surface of the wall contacts the feeding lumen, the interior surface of the wall and/or the first tube define an inflatable lumen having a proximal end and a distal end, the inflatable lumen extends longitudinally through at least a portion of the feeding lumen, and the wall is capable of allowing for deflation of the inflatable lumen through removal of a fluid and/or inflation of the inflatable lumen through introduction of a fluid into the inflatable lumen to change a volume of the feeding lumen, and wherein the first tube has a blockage. The method comprises (a) removing a fluid from and/or introducing a fluid into the proximal end of the inflatable lumen so as to change the volume of the feeding lumen; and (b) changing the pressure within the feeding lumen due to the change in volume of the feeding lumen thereby affecting the blockage in the tube. In a preferred embodiment, step (a) comprises first removing the fluid from the proximal end of the inflatable lumen, step (b) comprises decreasing pressure within the feeding tube and the method further comprises (c) inflating the inflatable lumen and increasing pressure within the feeding tube. It is also possible to repeat the steps of the method at least one additional time until the tube is unblocked.

Yet another embodiment of the invention includes a method for minimizing routine hospitalization and/or replacement of an enteral feeding device due to a blockage of the feeding device. The method comprises positioning an enteral feeding device in a patient which device comprises a first tube having a distal end and a proximal end, the first tube defining a feeding lumen that extends longitudinally through at least a portion of the first tube, the first tube having at least one distal opening capable of allowing introduction of nutrients and/or medicaments from within the feeding lumen through the opening into a gastrointestinal area of a patient when the enteral feeding tube is implanted in a patient; and a wall having a distal end and a proximal end, the wall extending longitudinally within at least a portion of the first tube, the wall having an exterior surface and an interior surface, wherein at least a portion of the exterior surface of the wall contacts the feeding lumen, wherein the interior surface of the wall and/or the first tube define an inflatable lumen having a proximal end and a distal end, wherein the inflatable lumen extends longitudinally through at least a portion of the feeding lumen, and wherein the wall is capable of allowing for deflation of the inflatable lumen through removal of a fluid from the inflatable lumen and/or inflation of the inflatable lumen through introduction of a fluid into the inflatable lumen to change a volume of the feeding lumen, and the change in the volume allows for a change in pressure in the feeding lumen that affects a blockage of the enteral feeding device.

BRIEF DESCRIPTION OF THE SEVERAL VIEWS OF THE DRAWING(S)

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings:

FIG. 1 is a perspective view of one embodiment of a J-tube;

FIG. 1A is a transverse cross-sectional view of the J-tube of FIG. 1 taken along line 1A-1A when the inflatable lumen is a deflated position;

FIG. 1B is a transverse cross-sectional view of the J-tube of FIG. 1 taken along line 1A-1A when the inflatable lumen is in an inflated position;

FIG. 1C is a transverse cross-sectional view of the J-tube of FIG. 1 taken along line 1C-1C;

FIG. 1D is a partially broken, partial longitudinal cross-sectional view of the J-tube of FIG. 1 in the area designated FIG. 1D;

Figure 8:
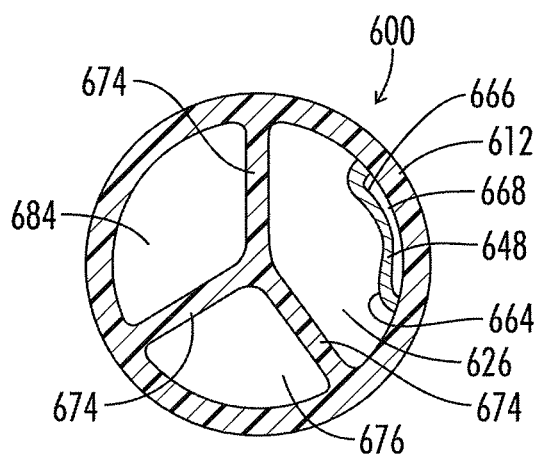
Figure 9:
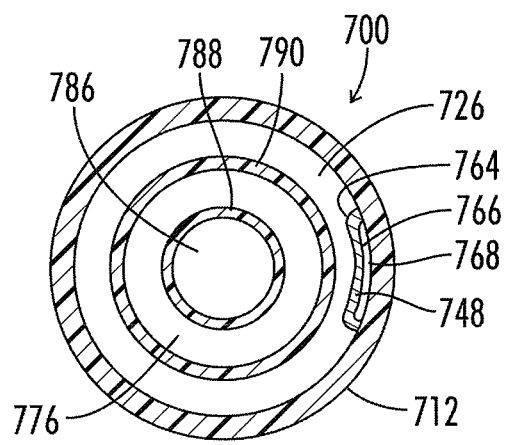
Figure 10:
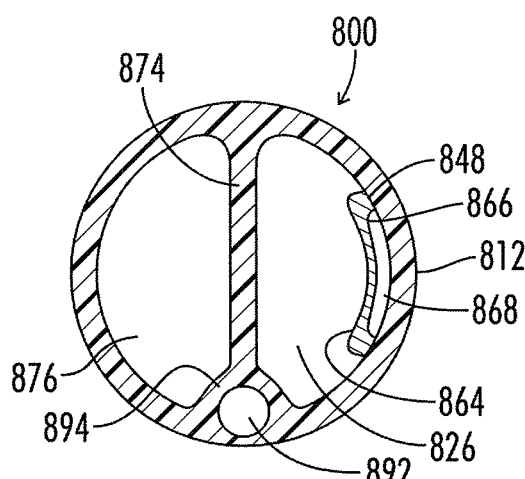
Figure 11:
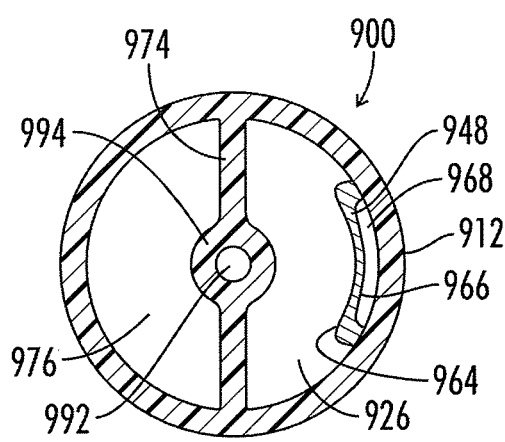
Figure 12:
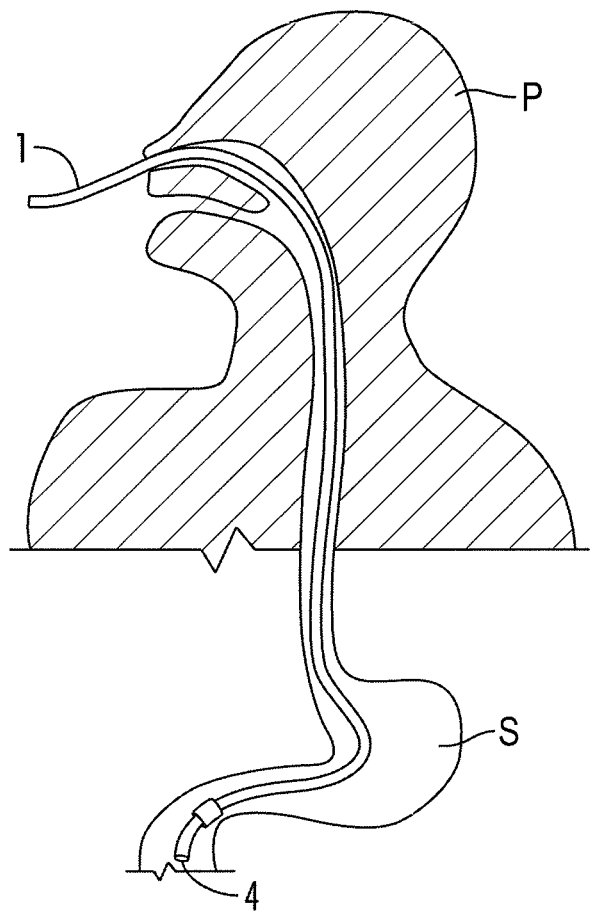
Figure 13:
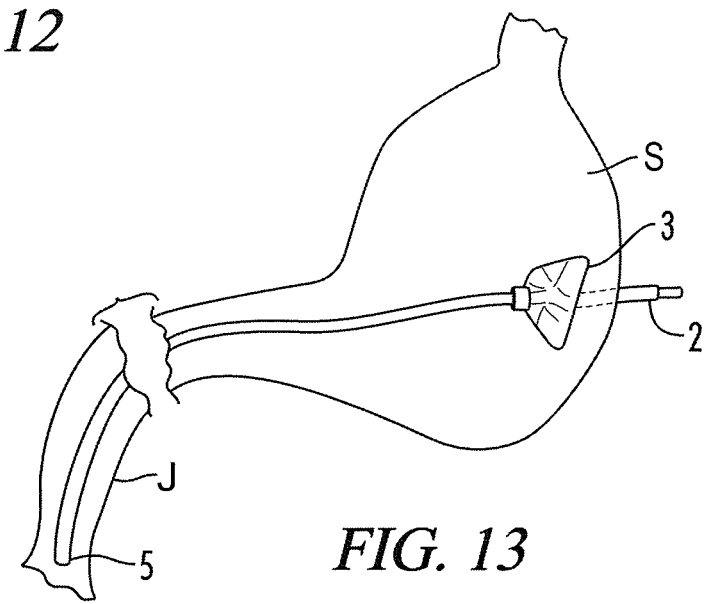
Figure 14:
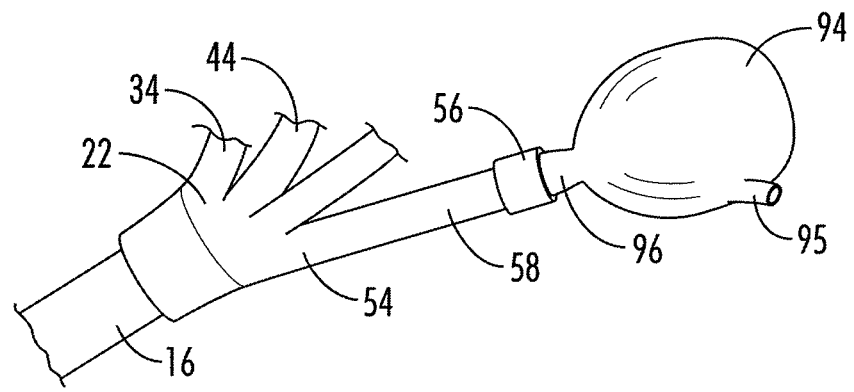
Figure 14A:
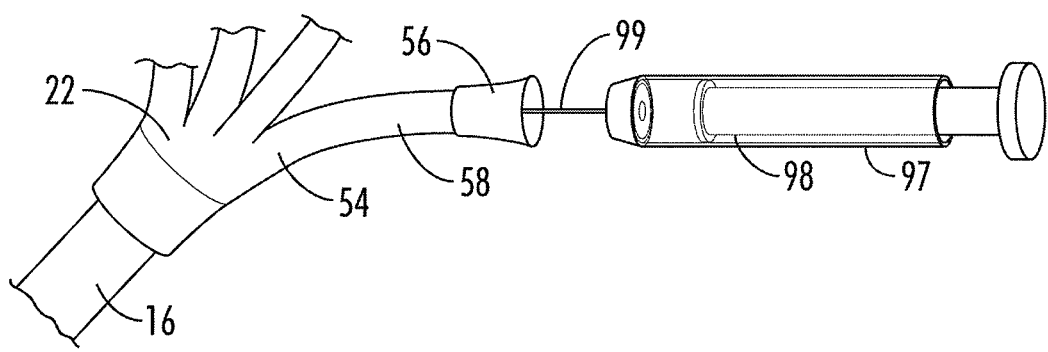
Figure 15:
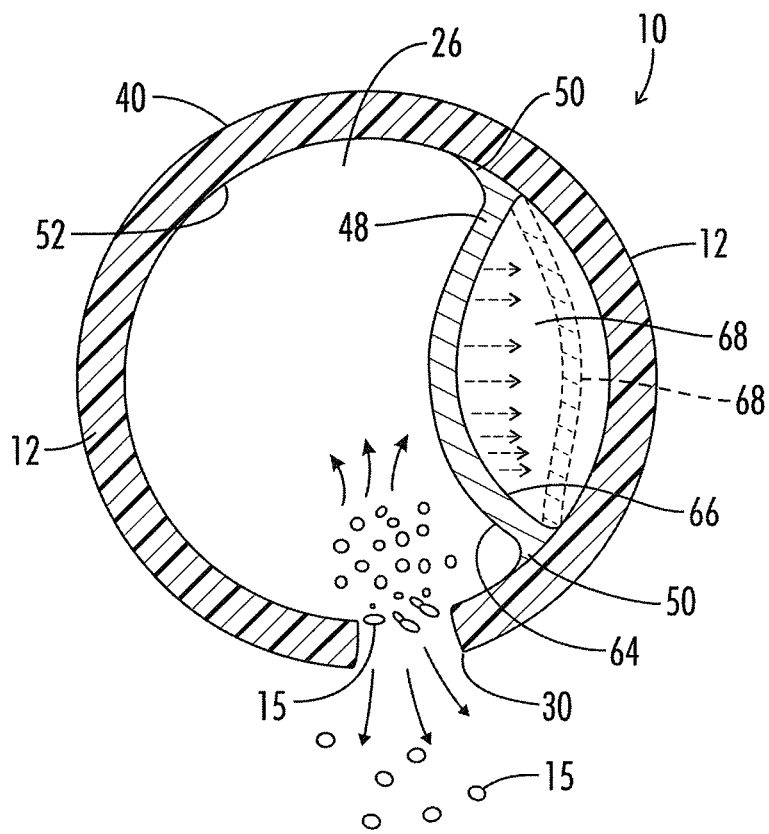
Figure 16:
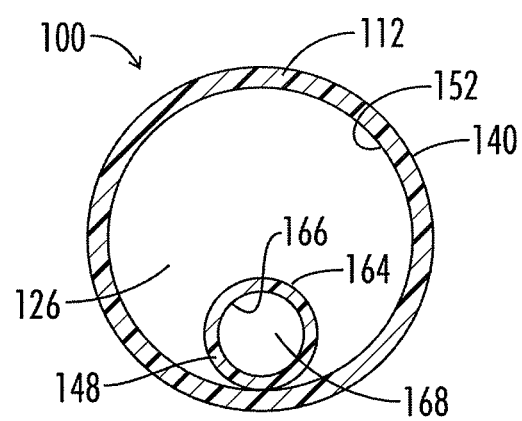

FIG. 8 an alternative representative transverse cross-sectional lumen configuration for an enteral feeding device according to another embodiment of the invention having a triple lumen configuration wherein each lumen is a wedge-shaped arcuate section;

FIG. 9 is an alternative representative transverse cross-sectional lumen configuration for an enteral feeding device according to another embodiment of the invention having a coaxial triple lumen configuration;

FIG. 10 is an alternative representative transverse cross-sectional lumen configuration for an enteral feeding device according to another embodiment of the invention having a triple lumen configuration wherein two of the lumens are side-by-side and one lumen has a circular cross-section and is located along one side of the other two lumens;

FIG. 11 is an alternative representative transverse cross-sectional lumen configuration for an enteral feeding device according to another embodiment of the invention having a triple lumen configuration wherein two of the lumens are side-by-side and one lumen having a circular cross-section is located within the septum dividing the other two lumens;

FIG. 12 is a representative view of the location of a nasogastric feeding tube having a distal end located within a stomach area of a patient;

FIG. 13 is a representative perspective view of the location of a G-tube within a patient's stomach and extending through a stoma, which may be extended such that the distal end can be placed in a patient's intestines;

FIG. 14 is a representative perspective view of a bladder-like device for deflating and/or inflating the inflatable lumen in the device of FIG. 1;

FIG. 14A is a representative perspective view of a syringe-like device for deflating and/or inflating the inflatable lumen in the device of FIG. 1;

FIG. 15 shows an enlarged transverse cross-sectional view of a blockage in a distal opening being unblocked by deflation of an inflated lumen, wherein the inflatable lumen is defined by a wall according to the invention; and FIG. 16 shows a transverse cross-sectional view of a tube-in-tube configuration for an inflatable lumen in a single lumen feeding tube in accordance with one embodiment of the invention.

DETAILED DESCRIPTION OF THE INVENTION

The invention will now be described with reference to the attached drawing Figures. Words such as "upper" and "lower," "interior" and "exterior," "inner" and "outer," and words of similar import are used herein for convenience purposes in viewing the drawings and are not meant to be limiting. "Proximal" and "distal," as used herein, are meant to describe portions of the device that are farther from and closer to the patient insertion end of the device.

The invention herein provides devices and methods for unclogging and/or preventing clogging of enteral feeding tubes. As used herein "enteral feeding tubes" can include within its scope a variety of feeding tubes that introduce nutrients, fluids and/or medicaments into a patient's gastrointestinal tract, including NG-tubes, J-tube and G-tubes. The devices are intended to be positioned in patients on-site (meaning at their local healthcare location, such as a hospital, convalescent home, long-term care facility, outpatient facility and the like) and can be used for long term care, while minimizing the occurrences of emergency hospitalization and/or patient discomfort associated with frequent changing out of such in-dwelling long-term care devices due to an enhanced feature to allow for easy on-site de-clogging of the device. This device serves as an alternative to prior art standard, routine flushing of the tube and/or replacement of the tube by the nurse or other health care professional. However, it should be understood that while flushing and/or replacement is minimized, ultimate long-term failure of such devices can still occur as materials used to form the devices deteriorate. It should be understood, however, that such materials can be varied and coatings included thereon to prevent deterioration.

The devices and/or methods described herein allow a health care professional to easily unclog a J-tube, G-tube, NG-tube or other enteral feeding tube with little disruption, inconvenience and discomfort to patients. It thus, minimizes the need to visit a hospital or clinic for replacement of the tubes.

In a first embodiment, the invention will be described with respect to a representative J-tube device as shown in FIG. 1. This is for illustrative purposes only and should not be considered limiting to the variety of devices that can incorporate the inventive features herein for reducing clogging. Other similar devices are shown in FIGS. 12 and 13 for use with the invention hereof. In FIG. 12, patient P has a nasogastric tube 1 which enters with the distal end passing through the nose and down the esophagus to be located in the stomach S as a gastrointestinal area and has a distal end 4 that feeds or supplies the stomach with materials. The proximal end then extends out of the nose. FIG. 13 shows stomach S with a G-tube that enters the stomach S through a stoma having an attachment 3 and a proximal end 2 that extends out of the stomach. The distal end 5 can be placed in the stomach (as in FIG. 12) or can be made to extend into the jejunum J as in FIG. 13. As shown in FIGS. 1, 1A, 1B and 1C, a long-term enteral feeding device in the form of a J-tube is used for providing details with respect to the invention. The J-tube device, generally referred to herein as 10, includes a first tube 12 which is a primary tube of the device 10. The tube 12 extends from a proximal end 14 along a proximal end portion 16 and a distal end 18 along a distal end portion 20. Upon insertion in a patient, the distal end portion 20 would be located in the patient's intestines, in a gastrointestinal area such as the jejunum. The proximal end 14 is located at the distal end of fitting portion 22. A cap 24, as is known in the art, can be located on the fitting portion 22 for capping the proximal end 14 of the first tube when not in use. In use, fluid, nutrients and/or medicaments may be introduced through open proximal end 14. The first tube 12 defines a feeding lumen 26 that extends through the first tube. The feeding lumen can be made in various embodiments to terminate in varied locations depending on how the patient is fed, however, for a J-tube as shown, it is preferred that the feeding lumen extends longitudinally through at least a portion of the first tube. The feeding lumen 26 preferably extends substantially through the first tube, and more preferably completely through the first tube from the proximal end 14 to the distal end 18 terminating in either a blunt end (or bolus) or a distal end opening. As shown, a distal end opening 28 is formed in the distal end.

The first tube has at least one distal opening, such as distal end opening 28, which is capable of allowing introduction of nutrients and/or medicaments from within the feeding lumen 26 through the opening 28 into a gastrointestinal area of a patient when the enteral feeding tube is implanted in a patient. However, as is common in the art, multiple openings may be located along the distal end portion 20 of the device 10, including multiple side-entry openings such as openings 30 to allow for ease of introduction of materials to the patient, and to provide multiple access ports should clogging of any one opening occur. In addition, further openings can be optionally provided on a more proximal location of the device 10 for introducing some materials to one gastrointestinal area (such as the stomach or another portion of the intestine) in addition to the gastrointestinal area being fed or treated by materials introduced through the distal end openings 28, 30. Examples of such additional, proximal openings are shown in FIG. 1 as openings 32.

Many such J-tubes also incorporate a standard inflation placement/securement balloon and inflation lumen for such placement/securement balloon, wherein the placement/securement balloon is used for locating and securing the device within the patient. Such lumens typically run through the wall of the first tube. While such a feature is optional it is shown herein for illustrative purposes. In FIG. 1, an inflatable placement/securement balloon 38 which can be glued or otherwise adhered to the exterior surface 40 of the first tube 12 which can have an opening 42 therethrough for introducing air, saline or other fluid into the inflatable placement/securement balloon 42. Fluid is introduced through an opening in a fitting end such as inflation fitting 34 in a manner known in the art and passes down an inflation lumen such as lumen 36 (see FIGS. 1 and 1A). Such inflation lumens typically terminate within the device structure at the end of the inflatable placement/securement balloon. Again, such a feature is optional and typically associated with certain types of J-tubes.

A gastric fluid withdraw fitting 44 is shown, although such a fitting is optional. Such fittings are sometimes used for suction withdraw of fluids from a patient's gastrointestinal areas when feeding or other intake of fluids is not occurring. Such fittings can be shut when not in use using any fitting cap, such as cap 46. It should be understood that the inclusion of an inflation lumen for placement/securement and/or a gastric fluid withdraw fitting are optional features that are common in the art and referred to herein for the purpose of describing a preferred embodiment only and should not be considered limiting features.

As seen in FIGS. 1 and 1A, a wall 48 is adhered on either end 50 to the interior surface 52 of the first tube so as to be placed within the feeding lumen 26. The wall 48 can extend along a portion of the length of any enteral feeding device, but it is preferred that the wall extends longitudinally along most, if not all of the length of the first tube 12. As shown, the wall 48 extends from an entrance point 54 within the fitting 22 at or near the proximal end portion 16 of the device 10 such that the entrance point 54 marks the proximal end 55 of the wall (alternatively, it may extend through entry tube 58 provided that it is blocked off separately from the feeding tube which extends through the main tube to the distal end 14 thereof. At point 54, the wall material may be adhered or be molded within the fitting so as to close off the proximal end 55 against the interior surface 52 of the first tube. However, it should be understood, that this placement is suggested so as to coincide with exemplary entrance tube 58 from example fitting 56 for introducing fluid. Suitable fluid for use in inflating the inflatable lumen 68 herein include such as air, water, or normal saline and other similar suitable inflation fluids that would be acceptable for such a use in the body provided that such fluid is able to inflate and deflate the lumen without rupturing the wall 48. The proximal end of the wall can be located further proximal along the device, further distally along the device, or at varied locations, but preferably, the proximal end of the wall is located along a portion of the first tube that would be located outside the patient's body so that fluid can be introduced for inflation from an external area of the device extending out of the patient. Methods for incorporating internal tubes within junction fittings communicating with external entry tubes as shown are known in the catheter arts and can be formed by insert molding, compression molding, heat molding using a mandrel and similar techniques known in the art.

The wall 48 further has a distal end 60 and the wall extends longitudinally within at least a portion of the first tube between its proximal end 55 and distal end 60. The distal end 60 is preferably located so as to be able to contribute to a change in volume and change in associated pressure within the feed lumen 26 somewhere along the length of the feeding lumen 26, wherein such change in pressure to be effected is sufficient as a result of the change in the interior volume of the feeding lumen to (by increasing and/or decreasing the allocable feeding lumen volume as described elsewhere herein) which then is able to affect a blockage in a manner that will allow for the unclogging of the tube, e.g., the loosening of a blockage within the body of the tube that passes normally out of the tube or the loosing of a blockage in the distal openings 28, 30.

The wall can be deflated and/or inflated to change the volume and thereby change the pressure within the feeding tube and affect a blockage or clog. It is preferred that the long-term feeding tube device includes the wall and inflatable lumen in an inflated position prior to use. The inflatable lumen can be fully or at least partially inflated with any fluid as noted elsewhere herein. The feeding lumen and inflatable lumen are sized such that it is preferred that when the inflatable lumen is fully inflated, the remaining volume of the feeding tube comports with what is acceptable in the medical industry for providing adequate fluid/nutrients/medicaments through a feeding tube and for fitting comfortably within a patient, including any preferred feeding tube dimensions in terms of internal cross-sectional area. In use, should a clog occur, the blockage causing the clog may be affected by first deflating the inflatable lumen in whole or in part to thereby increase the feeding lumen volume (and thereby decrease pressure within the tube). This allows for the blockage which was previously under pressure within the feeding tube to preferably break apart and disperse due to the increase in volume (which aids in creating a pressure gradient within the fluid in the feeding tube that helps to pull the particles in the blockage apart). If the blockage is not sufficiently affected so as to dislodge the blockage and unclog the feeding tube by simply deflating the inflatable lumen, the lumen can be reinflated thereby increasing pressure in the feeding tube and decreasing the volume in the feeding tube to once again put pressure on the remaining blockage. This process can be repeated to cause expansion and contraction of the inflatable lumen that allows for continued change in volume of the feeding tube and pressure in the feeding tube so as to continue to internally affect the blockages until de-clogging of the tube and/or any clogged distal openings is effected. Preferably, the initial deflation of the inflatable lumen creates enough change to affect the blockage and unclog the feeding tube, however, it would be understood that for some blockages, additional aspiration of the inflatable lumen from deflation to inflation would be required to affect the blockage and unclog the feeding tube. The change in volume and pressure can thereby act to push and pull particles or other objects in the openings to dislodge them from a compacted blockage form in the tube and/or in the distal opening holes. It will be understood that this device and the unclogging techniques noted above using such device can work alone or can be used in combination with other unclogging techniques known in the art.

As shown, the wall extends through the first tube down to within the distal portion 20 in the location of the distal side openings such that the distal end of the wall would be located around distal end location 62. At that location, the distal end 60 of the wall 48 would be sealed or otherwise affixed to the interior surface 52 of the first tube to close off the wall. The wall can also be made to extend further to the distal end opening 28 provided it does not block the end opening. It is preferable that it not extend all the way to the end opening 28 to avoid interfering with the end opening, however, it should be understood based on this disclosure that the wall can extend to wherever it would best optimize unclogging performance for a given design without significantly impacting the flow or delivery of medicaments, nutrients and/or fluids to a patient.

The wall has an exterior surface 64 and an interior surface 66. At least a portion of the exterior surface of the wall contacts the feeding lumen such that it acts to divide the feeding lumen 26 from the interior space of inflatable lumen 68. The interior surface 66 of the wall and/or the first tube, typically by way of interior surface 52 of the first tube 12 can define the inflatable lumen 68. Thus, the lumen 68 can be wholly defined as within the interior surface 66 of the wall (such as if the wall forms a separate lumen) or can be formed as is more preferable by attaching, affixing, molding or otherwise adhering the wall 48 along its length to the interior surface 52 of the first tube 12 (and to the interior surface of fitting 22 if necessary). Thus, the inflatable lumen 68 can extend from its proximal end 70 to its distal end 72 which are reasonably coextensive with the proximal end 55 of the wall and the distal end 60 of the wall (although slightly shorter in length in that the ends of the wall are adhered to the first tube 12. The inflatable lumen 68 extends longitudinally through at least a portion of the feeding lumen 26 and generally along the length of the wall 48 as noted above. The wall 48 is capable of allowing for deflation of the inflatable lumen through the removal of fluid from the inflatable lumen and/or inflation of the inflatable lumen through introduction of a fluid into the inflatable lumen. Fluid can be removed and/or introduced through the proximal end 70 of the lumen. To do so, fluid can be removed and/or introduced, for example, through fitting 56, tube 58 attached at location 54, and then through the proximal end 70 of the lumen 68. The deflation of an already inflated inflatable lumen 68 changes the volume of the feeding lumen 26 as can the inflation of the inflatable lumen 68 as described above.

In various embodiments herein, the enteral feeding device may have a first tube of a wide variety of configurations. As shown in FIG. 1, the first tube has a single lumen feeding tube over most of its length (with the exception of a minor inflation lumen in the distal end thereof for inflating placement balloon 38). However, various alternative lumen configurations are contemplated herein for use with a wide variety of G-tubes, J-tubes and NG-tubes that exist or maybe developed in the art. A variety of examples is shown herein, and should not be considered limiting.

For example, as shown in FIG. 16, a cross-section of a device 100 has a first tube 112 defining a first feeding lumen 126 that includes a tube-within-a-tube configuration (i.e., it has at least a second tube formed by a wall 148 and defining inflatable lumen 168 (shown expanded therein). Such a wall can be adhered along its length in a longitudinal bead or weld along the length of the wall. The interior surface 166 of the wall 148 defines the inflatable lumen 168 extant of the interior surface 152 of the first tube 112. The wall 148 forms a tube extending longitudinally within the feeding lumen 126.

Figure 2:
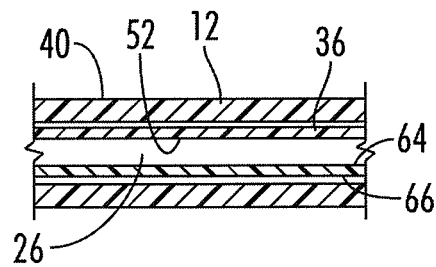
FIG. 2 is a partially broken, enlarged longitudinal cross-sectional view of the J-tube of FIG. 1 in the area designated FIG. 2.
Figure 3:
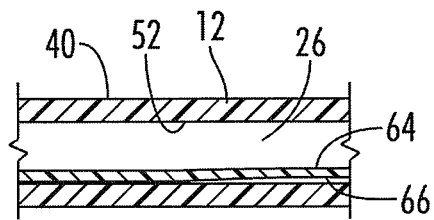
FIG. 3 is a partially broken, enlarged longitudinal cross-sectional view of the J-tube of FIG. 1 in the area designated FIG. 3.
Figure 3A:
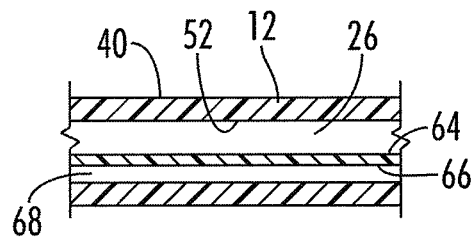
FIG. 3A is a partially broken, enlarged longitudinal cross-sectional view of the area of FIG. 3 when the inflatable lumen is inflated.
Figure 4:
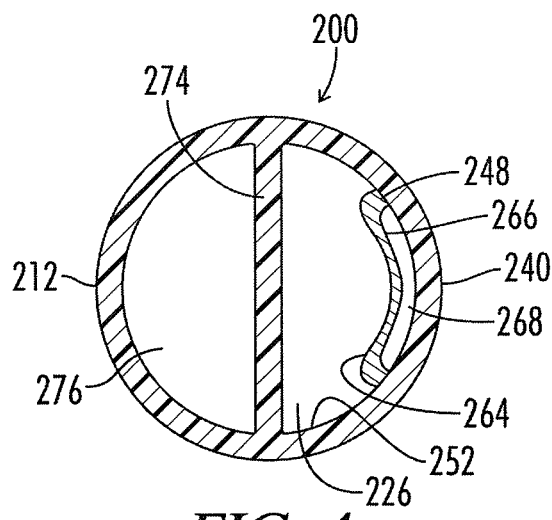
FIG. 4 is an alternative representative transverse cross-sectional lumen configuration which can be taken for example along line B-B for an enteral feeding device according an embodiment of the invention having a side-by-side dual lumen configuration.
Figure 5:
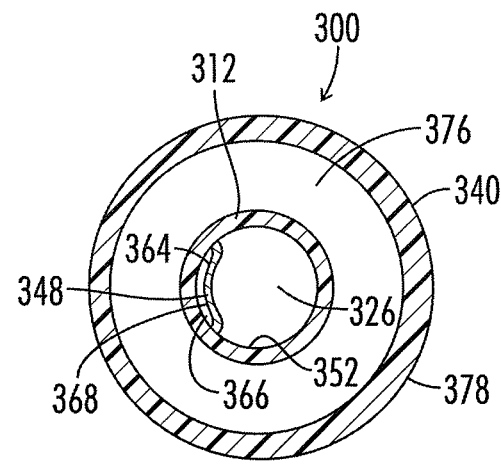
FIG. 5 is an alternative representative transverse cross-sectional lumen configuration for an enteral feeding device according to another embodiment of the invention having a coaxial dual lumen configuration.
Figure 6:
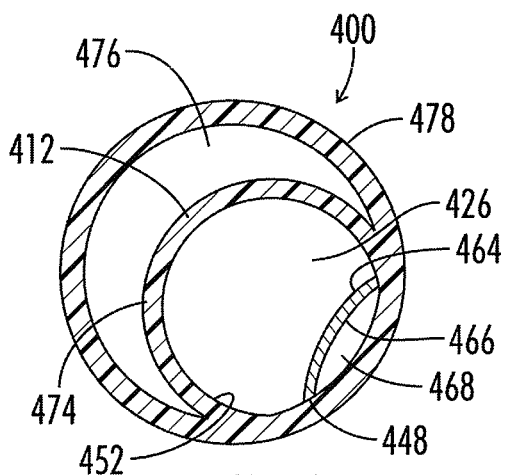
FIG. 6 is an alternative representative transverse cross-sectional lumen configuration for an enteral feeding device according to another embodiment of the invention having a circle-C dual lumen configuration.

As shown in FIGS. 4, 5 and 6, the devices herein may be dual lumen devices having at least two functioning lumens as well as a wall and inflatable lumen for unclogging blockages. As in FIG. 4, a cross-section of a representative device 200 is shown wherein two lumens, one of which is a feeding lumen 226 and the other of which 276 may be another feeding lumen, a lumen strictly for medicaments, a lumen for introducing heparin, withdrawing gastric fluids, etc. The uses are not limited herein. However, it is preferred that the inflatable lumen 268 and the wall 248 be placed in a lumen which is a feeding lumen and/or which is a lumen that could have a clogging problem for whatever reason (herein identified as a feeding lumen, but that term should not restrict such lumens to be "feeding" lumens—as a number of substances may be introduced therein and such lumen is primarily identified as a lumen which may have a clogging problem, typically such lumens are associated with feeding nutrients). As shown, the feeding lumen (clogging lumen) is on the right hand side, however, it should be understood that the lumens could be reversed and the feeding lumen and wall placed on the left hand side instead or that a wall and inflatable lumen such as lumen 268 can be located in both lumens 226, 276 of the device 200. It is also noted that a septum 274 is provided to divide the dual lumens in a way known to those skilled in the art. Such septa can be provided through integral unitary molding of the tube or incorporated as an insert molded or glued/adhered feature. However, it is most common to mold a septum as integral to the tube 212. The septum preferably extends longitudinally along at least a portion of the length of the first tube, and typically extends through substantially all of the tube culminating in separation and the end of one of the lumens at or near the distal end of the tube.

As shown in FIG. 4, the first tube has two side-by-side D-shaped lumens. However, in FIG. 5, two coaxial lumens are shown in representative cross section of a device 300. In device 300, the first tube 312 that defines the feeding lumen 326 is in the interior of the coaxial lumen configuration and another tube wall 378 defines second lumen 376. The feeding lumen 326 incorporates the wall 348 having exterior surface 364 and interior surface 366 and inflatable lumen 368. Such coaxial lumen configurations can be made using various techniques known or to be developed in the art, and as noted with respect to FIG. 4, the outer and inner lumen configuration can be reversed in FIG. 5 such that the outer lumen 376 could be made to be the feeding lumen, the outer tube 378 could be the first tube and the wall could be located within tube 378. Additionally, two such walls could be used, one in each lumen if clogging were a problem in both lumens. The second lumen 378 can be used for a variety of purposes as noted above with respect to the second lumen in FIG. 4.

FIG. 6 shows a cross-section of a representative device 400 having two lumens in a "circle-C" configuration. As shown, like FIG. 5, the feeding lumen 426 is within the inner tube 412 which is also a septum 474 between the first and second lumens. However, the feeding lumen could be switched to be in the outer lumen 476 defined by outer tube 478 or both tubes 412 and 478 could define feeding lumens. In this configuration wall 448 is located within tube 412 and has inflatable lumen 468.

FIGS. 7-11 show various triple lumen designs. It is preferred that for a triple lumen configuration, at least one of the lumens be a feeding lumen, however, two of the lumens or three of the lumens may be feeding lumens.

Figure 7:
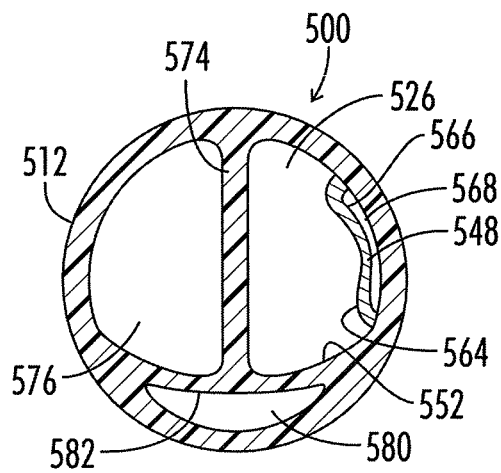
FIG. 7 is an alternative representative transverse cross-sectional lumen configuration for an enteral feeding device according to another embodiment of the invention having a triple lumen configuration wherein two of the lumens are side-by-side and one lumen is semi-circular in cross-section.

In FIG. 7, a representative device cross-section is shown of device 500 having three lumens, feeding lumen 526, second lumen 576 in a side-by-side arrangement with lumen 526 and a third lumen 580 having a generally semi-circular configuration. Such lumens can deliver the same or different materials than feeding lumen 526 which typically would introduce nutrients, medicaments and/or fluids to a patient. Third lumen 580 is formed by a second septum 582 formed at one end of the other two lumens 526, 576 that intersects primary septum 574. As shown, the feeding lumen 526 is on the right hand side and has inflatable lumen 568, but a wall such as wall 548 can be formed also in lumen 576 or lumen 580, or all three lumens if clogging presents an issue therein.

FIG. 8 shows a representative cross-sectional configuration of a device 600 using triple lumens in an equally spaced, arcuate wedge-shaped lumens, wherein one of the three lumens is feeding lumen 626. The other two lumens 676 and 684 are defined by equal dividing septa 674 extending to a center point. The inflatable lumen 668 is shown in lumen 626, however, such a lumen may be in either or both of the other two lumens, 676, 684.

FIG. 9 shows a cross-sectional view of a representative device 700 having a triple coaxial lumen configuration, wherein at least one of the three lumens is the feeding lumen. As shown, the three lumens 726, 776, and 786 are defined by three coaxial tubes, including first tube 712 on the exterior of the device 700, such that inflatable lumen 768 is within the feeding lumen 726 and on the outer lumen of the coaxial device 700. Two inner lumens 776 and 786 are defined between tubes 790 and 788 and within tube 788 respectively. Such tubes may be joined using triple coaxial manufacturing techniques and designs known in the art or to be developed. As shown, the feeding lumen and the inflatable lumen are in outer tube 512, however, it should be understood that the feeding lumen may be middle lumen 776 or inner lumen 786 and that all can be feeding lumens (i.e., lumens which may clog). Further, an inflatable lumen 768 and wall 748 may be provided in one, two or three of the lumens of the triple coaxial design.

FIG. 10 shows a cross-section of a representative device 800 having a feeding lumen 826 defined on a right hand side of tube 812, wherein tube 812 is divided in part by septum 874 and further by septum 894 to provide a second lumen 876 (in side-by-side arrangement with lumen 526) and a third lumen 892 which has a generally circular cross-section. Such smaller triple lumens can be used for introducing fluids and also as a bypass lumen when clogging occurs, for guidewire or de-kinking devices (such as rods and the like). As shown, feeding lumen 526 is on the right hand side, but it could also be on the left hand side. In addition, one, two or all three lumens may have a wall 848 and an inflatable lumen 868, however, it is not preferred to provide such a wall to a smaller lumen such as lumen 892 due to manufacturing constraints.

FIG. 11 shows a representative device 900 in cross-section which is similar to device 800 of FIG. 10, however, the smaller lumen 992 is located as an expanded septum 994 that is formed within septum 874. In other respects the device would be similar to that of FIG. 10.

Other various multilumen configurations known in the art or to be developed can be used with a wall such as wall 48 and inflatable lumen 68 as taught herein, so as to incorporate such structures in lumens that may clog due to introduction of medicaments, nutrients, fluids or operation of the patient's body. As used herein, it is preferred that such wall and inflatable lumen structures be incorporated within "feeding lumens," which as used herein means a lumen that can include an opening therethrough for introduction of fluids, medicaments, nutrients or other materials and/or which experiences blockage, such that the inflatable lumen and wall herein can be deflated and/or inflated to create a change in volume in the feeding lumen to affect a blockage and assist in unblocking a clogged tube or tube opening.

In making the tubes and other body components of the G-tubes, J-tubes and the like herein, it is within the scope of the invention to include reinforcing materials (metals, and composite fillers) within the materials used to make any of the embodiments of the first tube and other optional tubes, septa and related features of the device where indicated. In addition, additives for sterility (such as silver and the like) and for radiopacity may also be incorporated. Septum wall reinforcing metallic strips can also be used herein. The materials used to make the structural components may be those known in the art or to be developed for G-tube, J-tube, NG-tubes and other similar devices, such as various types of catheter tubing. Such materials may be formed, for example, from conventional elastomeric polyurethanes such as those sold under the trademarks ESTANE and PELLETHANE from B. F. Goodrich and Dow Chemical Company, respectively. Other polymeric materials such as polyvinyl chloride, styrenic polymers such as KRATON®, polyacrylates, polyolefins, polyamides, polyesters, fluoropolymers, silicones, polyphosphazenes, perfluoroelastomers, fluroelastomers, and copolymers, derivatives, blends and alloys of such polymers may be used. Such materials are conventionally employed in the art to prepare such devices, and can be employed to fabricate the tubular components by extrusion, insert molding, mandrel techniques and other various methods. Coatings for strengthening, sterilization, radiopaque, acid-resistance and other special properties and additives as well to achieve such properties may also be used, such as poly(p-xylene) polymer as described in WO 95/04564 incorporated with respect to the description of use of such polymer herein.

In various embodiments herein, the wall is preferably made of a flexible polymeric material. Such materials are known in the art and can include polyurethanes, polyamides (such as nylon-12), polyether block amides (such as the material sold under the trademark PEBAX), polyethylene, and polyethylene terephthalate, polybutylene terephthalate, polyester elastomers including those that use a polyester as a hard segment, polyolefins (such as polyethylene, polypropylene, polybutylene and combinations and co-polymers thereof), polyolefin elastomers, vinyl-based polymers (such as polyvinyl chloride, polyvinylidene chloride, or polyvinylidene fluoride), polyamide elastomers, polyimides, polystyrenes, styrene-ethylene/butylene-styrene resins, polyurethane elastomers, acrylonitrile-butadiene-styrene resins, acrylic resins, polyarylates, polycarbonates, polyoxymethylenes, polyvinyl alcohol, and fluorocarbon resins, such as ethylenetetrafluoroethylene, perfluoroalkoxy copolymer, polytetrafluoroethylene, fluoroelastomers, perfluoroelastomers, and copolymers, derivatives, combinations, alloys and the like of these materials, provided that the property of the material should be selected so as to be capable of being adhered to the interior wall of at least the first tube and being inflated without breaking upon introduction of a fluid, such as water, saline, air, etc. into the inflatable lumen lying, preferably prior to use, and then lying substantially flat along the wall when fluid is removed to change the volume within the feeding tube. Such materials are known in the art and are preferably the same as are traditionally used to make the placement/securement balloon used on traditional J-tubes and G-tubes and/or that are used on angioplasty catheters having expandable balloons used in heart treatment, or expandable balloons used in hemodialytic catheters. The material used to form the wall 48 may be adhered to the interior surface of the first tube 12 by any suitable glue, or heat molding or heat-welding process, as well as through a tie-layer polymer that molds the wall 48 to the interior surface of the tube 12.

The enteral feeding device may further include a detachable or permanently attached device as shown in FIGS. 14 and 14A for inflating the inflatable lumen 68. FIG. 14 shows an example of a compressible bladder in the form of a hand-held bulb 94 which can be attached through a stem or other entry device such as stem 96 into fitting 56. A bleed valve 95 is optionally included for depressing and expelling air for hand-pumping air into the fitting 56 through tube 58 and into the proximal end of the inflatable lumen 68. Other compressible bladders may be used in communication with the proximal end of the inflatable lumen for introduction of fluid for inflation and deflation of the inflatable lumen. Alternatively, the fitting 56 may be formed so as to be capable of receiving an injected fluid through a lumen of a needle 99 through a septum or other surface wherein the fluid enters the needle through a syringe 97 having a plunger 98 therein. Pressure on the plunger introduces fluid into the fitting. An air or fluid pump or any other air or fluid source capable of introducing or withdrawing, and preferably of aspirating fluid within the inflatable lumen may be used.

A method for unclogging an enteral feeding device, such as device 10, when implanted in a patient is also provided. The enteral feeding device should be made in accordance with the disclosure hereinabove, and can include any of the variations of lumen configurations and types of enteral feeding devices described herein, preferably, the device includes the features of device 10 described herein. The method includes removing and/or introducing a fluid into a proximal end of an inflatable lumen, such as proximal end 70 of inflatable lumen 68 herein so as to change the available volume within a feeding lumen as described herein, preferably a feeding lumen such as lumen 26. A change in pressure is thus effected within the lumen of the feeding lumen due to the change in volume of the feeding lumen in the feed tube. The change in volume and pressure affects a blockage in the feeding lumen so as to push or pull the blockage and particles which may be within the blockage allowing the blockage to break free and move through the lumen and/or exit a distal end opening 28 or various openings such as openings 30 in device 10, thereby unclogging the feeding lumen and/or distal openings. The method may further include using an enteral feeding device, wherein the inflatable lumen is preferably but not necessarily inflated prior to positioning the device in the patient using any suitable medical technique for inserting and/or positioning and/or implanting a feeding tube. It should understood that the device can be inflated before or after placement in the patient. When a blockage is present, the inflatable lumen is deflated to change the volume in the feeding lumen of the feed tube by increasing the volume such that pressure is reduced. If this does not completely dislodge the blockage, the inflatable lumen may be inflated again to again change the volume in the feeding lumen (decrease volume) and increase pressure therein. The series of steps deflating, inflating and deflating can be repeated one or more times by aspirating or otherwise introducing and withdrawing fluid from the inflatable lumen to help dislodge blockages in the feeding tube and/or distal opening(s) of the enteral feeding device, and to ensure the tube and/or distal opening(s) is/are unblocked.

Fluid may be introduced in this method through a syringe, bladder or the like and the pressure in the feeding lumen increases or decreases as the syringe, bladder or other device is depressed, extended or otherwise aspirated. While the procedure is described in one preferred embodiment as beginning with a fully inflated lumen for convenience purposes, it is within the scope of the invention to begin the process with a deflated lumen and inflate the lumen upon occurrence of a blockage as well, and to continue to deflate and inflate, as needed to dislodge a blockage and unclog the feeding tube and/or its openings.

As shown in FIG. 15, taken along line 15-15 in FIG. 1 through an area near a distal opening 30, the inflatable lumen 68 is initially inflated such that space wall 48 extends into the interior of the device providing an acceptable volume in the feeding lumen 26 for feeding, hydrating and/or introducing medication to a patient. A blockage of particles 15 is shown initially within the feeding lumen 26 which is also near a distal opening 30 (however, such a blockage can occur throughout the feeding lumen). The inflatable lumen is deflated as shown by the phantom lines and the volume within the feeding lumen thereby increases by the amount made available to the feeding lumen by movement of the wall 48 and deflation of the inflatable lumen 68. This allows for a decrease in pressure within the feeding lumen 26 allowing for particles 15 in the blockage to move in towards the interior so as to break up the blockage leaving some particles 15 to move outward through distal opening 30 within the fluid and/or air from the feeding tube. Thus the particles 15 are unblocked and the feeding lumen and opening 30 can be unclogged. If the blockage were not fully removed, the lumen 68 can be again inflated using a bulb or syringe, etc., and the volume within the feeding tube 26 would suddenly decrease again, increasing the pressure which would cause further pushing of particles 15 toward the distal opening and/or movement within the feeding lumen. The process can continue to push and pull particles into and out of the center of the feeding lumen and in and/or out of the opening 30 as the change in volume and pressure work to affect the particles 15 in the blockage and to unclog the feed tube and the opening 30.

A method for minimizing routine hospitalization and/or replacement of an enteral feeding device is also provided herein, wherein an enteral feeding device is positioned within a patient. The device may be positioned in the patient using a variety of techniques known in the art, and no special techniques for insertion are required as a result of the inclusion of the inflatable lumen and wall herein. The enteral feeding device in this method is preferably that as described herein which has a wall and an inflatable lumen, such as device 10 with wall 48 and inflatable lumen 68 as described hereinabove. The wall is preferably capable of allowing for deflation and/or inflation of the inflatable lumen through withdrawal of a fluid out of or introduction of a fluid into the inflatable lumen to change a volume of the feeding lumen causing a change in pressure such that the inflatable lumen affects the blockage and thereby allows for unclogging of the enteral feeding device.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. An enteral feeding device, comprising:
   a first tube having a distal end and a proximal end, the first tube defining a feeding lumen that extends longitudinally through at least a portion of the first tube, the first tube having at least one distal opening capable of allowing introduction of nutrients and/or medicaments from within the feeding lumen through the opening into a gastrointestinal area of a patient when the enteral feeding tube is implanted in a patient, wherein the at least one distal opening comprises a distal end opening; and
   a wall having a distal end and a proximal end, the wall extending longitudinally within at least a portion of the first tube, the wall having an exterior surface and an interior surface, wherein at least a portion of the exterior surface of the wall contacts the feeding lumen and the interior surface of the wall defines an inflatable lumen having a proximal end configured to receive or remove an inflation fluid therethrough and a closed distal end, wherein the inflatable lumen extends longitudinally through at least a portion of the feeding lumen, and wherein the wall is capable of allowing for deflation of the inflatable lumen through removal of a fluid from the inflatable lumen and/or inflation of the inflatable lumen through introduction of a fluid to effect a change in a volume and pressure of the feeding lumen for dislodging a clog or blockage and allows for flow or delivery of medicaments, nutrients and/or fluids to a patient and the inflatable lumen is sized such that when fully inflated a volume of the feeding lumen in the feeding tube allows for adequate flow of fluid and/or medicament and/or nutrient to a patient.

2. The enteral feeding device according to claim 1, wherein the feeding tube is a single feeding lumen.

3. The enteral feeding device according to claim 2, wherein the first tube comprises at least a second tube extending longitudinally within the feeding lumen outside of the inflatable lumen along at least a portion of a length of the first tube.

4. The enteral feeding device according to claim 1, wherein the first tube has at least two lumens in addition to the inflatable lumen, each of the at least two lumens defined by at least one septum extending longitudinally along at least a portion of a length of the first tube, wherein at least one of the lumens within the first tube is the feeding lumen.

5. The enteral feeding device according to claim 4, wherein the first tube has two side-by-side D-shaped lumens, at least one of which is the feeding lumen.

6. The enteral feeding device according to claim 4, wherein the first tube has two lumens in a circle-C configuration, at least one of which is the feeding lumen.

7. The enteral feeding device according to claim 4, wherein the first tube has two coaxial lumens, at least one of which is the feeding lumen.

8. The enteral feeding device according to claim 4, wherein the first tube has three lumens, wherein two of the three lumens are side-by-side arcuate wedge-shaped lumens and one of the three lumens has a semi-circular configuration, wherein at least one of the three lumens is the feeding lumen.

9. The enteral feeding device according to claim 4, wherein die first tube has three coaxial lumens, wherein at least one of the three lumens is the feeding lumen.

10. The enteral feeding device according to claim 4, wherein the first tube has three equally spaced arcuate lumens, wherein at least one of the three lumens is the feeding lumen.

11. The enteral feeding device according to claim 4, wherein the first tube has three lumens, wherein two of the three lumens are side-by-side lumens and one of the three lumens has a circular cross section and is located either along an interior surface of the first tube or is defined by the septum between the two side-by-side lumens.

12. The enteral feeding device according to claim 1, wherein the feeding lumen extends along a trill length of the first tube.

13. The enteral feeding device according to claim 1, wherein the distal end of the first tube has a plurality of the distal openings.

14. The enteral feeding device according to claim 1, wherein the first tube is a gastrostomy tube.

15. The enteral feeding device according to claim 1, wherein the first tube is a jejunostomy tube.

16. The enteral feeding device according to claim 1, wherein the wall comprises a flexible material and the enteral feeding device further comprises a compressible bladder in communication with the proximal end of the inflatable lumen for removal or introduction of fluid and/or air for deflation and inflation of the inflatable lumen.

17. The enteral feeding device according to claim 1, wherein the wall comprises a flexible material and the enteral feeding device further comprises a fitting and is located on the device so that the fitting is in fluid communication with the proximal end of the inflatable lumen and the fitting is capable of allowing passage of an injected fluid therethrough for removing the fluid from the inflatable lumen for deflation thereof or for introducing the fluid into the inflatable lumen for inflation thereof.

18. The enteral feeding device according to claim 1, wherein the interior surface of the wall defines the inflatable lumen.

19. The enteral feeding device according to claim 1, wherein the interior surface of the wall together with an interior surface of the first tube defines the inflatable lumen.

20. The enteral feeding device according to claim 1, wherein the inflatable lumen extends from the distal end of the feeding lumen to the proximal end of the feeding lumen.

21. The enteral feeding device according to claim 1, further comprising a fluid within the inflatable lumen.

22. An enteral feeding device, comprising:
a first tube having a distal end and a proximal end and having a length measured longitudinally therebetween, the first tube defining a feeding lumen that extends longitudinally through the first tube, the first tube having at least one distal opening capable of allowing introduction of nutrients and/or medications from within the feeding lumen through the opening into a gastrointestinal area of a patient when the enteral feeding tube is implanted in a patient, wherein the at least one distal opening comprises a distal end opening; and
a wall having a distal end and a proximal end and a length measured longitudinally therebetween, the wall extending longitudinally from the distal end of the first tube for at least a portion of the length of the first tube, the wall having an exterior surface and an interior surface, wherein at least a portion of the exterior surface of the wall contacts the feeding lumen, wherein the interior surface of the wall defines an inflatable lumen having a proximal end configured to receive or remove an inflation fluid therethrough and a closed distal end, wherein the inflatable lumen extends along the length of the wall, and wherein the wall comprises a flexible material capable of allowing for deflation of the inflatable lumen through removal of a fluid from the inflatable lumen and/or inflation of the inflatable lumen through introduction of a fluid into the inflatable lumen to change a volume and pressure of the feeding lumen for dislodging a clog or blockage and allows for flow or delivery of medicaments, nutrients and/or fluids to a patient and the inflatable lumen is sized such that when fully inflated a volume of the feeding lumen in the feeding tube allows fir adequate flow of fluid and/or medicament and/or nutrient to a patient.

23. The enteral feeding device according to claim 22, wherein the feeding device is at least one of a gastrostomy tube and a jejunostomy tube.

24. A method for unclogging an enteral feeding device when implanted in a patient, wherein the enteral feeding device comprises a first tube having a distal end and a proximal end and defining a feeding lumen that extends longitudinally through at least a portion of the first tube, wherein the first tube has at least one distal opening capable of allowing introduction of nutrients and/or medicaments from within the feeding lumen through the opening into a gastrointestinal area of a patient when the enteral feeding tube is implanted in a patient; and a wall having a distal end and a proximal end, the wall extending longitudinally within at least a portion of the first tube, and having an exterior surface and an interior surface, wherein at least a portion of the exterior surface of the wall contacts the feeding lumen, the interior surface of the wall defines an inflatable lumen having a proximal end configured to receive or remove an inflation fluid therethrough and a closed distal end, the inflatable lumen extends longitudinally through at Least a portion of the feeding lumen, and the wall is capable of allowing for deflation of the inflatable lumen through removal of a fluid and/or inflation of the inflatable lumen through introduction of a fluid into the inflatable lumen to change a volume and pressure of the feeding lumen and allows for flow or delivery of medicaments, nutrients and/or fluids to a patient, the inflatable lumen being sized such that when fully inflated a volume of the feeding lumen in the feeding tube allows fir adequate flow of fluid and/or medicament and/or nutrient to a patient, and wherein the first tube has a blockage, the method comprising:
(a) removing a fluid from and/or introducing a fluid into the proximal end of the inflatable lumen so as to change the volume of the feeding lumen; and
(b) changing the pressure within the feeding lumen due to the change in volume of the feeding lumen thereby affecting the blockage in the tube.

25. The method according to claim 24, wherein step (a) comprises first removing the fluid from the proximal end of the inflatable lumen, step (b) comprises decreasing pressure within the feeding tube and the method further comprises (c) inflating the inflatable lumen and increasing pressure within the feeding tube.

26. The method according to claim 25, comprising repeating the steps of the method at least one additional time until the tube is unblocked.

27. The method according to claim 24, wherein the fluid is removed and/or introduced through a syringe.

28. The method according to claim 24, wherein the fluid is removed and/or introduced through a bulb.

29. A method for minimizing routine hospitalization and/or replacement of an enteral feeding device due to a blockage of the feeding device, the method comprising
positioning an enteral feeding device in a patient which device comprises a first tube having a distal end and a proximal end, the first tube defining a feeding lumen that extends longitudinally through at least a portion of the first tube, the first tube having at least one distal opening capable of allowing introduction of nutrients and/or medicaments from within the feeding lumen through the opening into a gastrointestinal area of a patient when the enteral feeding tube is implanted in a patient; and a wall having a distal end and a proximal end, the wall extending longitudinally within at least a portion of the first tube, the wall having an exterior surface and an interior surface, wherein at least a portion of the exterior surface of the wall contacts the feeding lumen, wherein the interior surface of the wall defines an inflatable lumen having a proximal end configured to receive or remove an inflation fluid therethrough and a closed distal end, wherein the inflatable lumen extends longitudinally through at least a portion of the feeding lumen, and wherein, the wall is capable of allowing for deflation of the inflatable lumen through removal of a fluid from the inflatable lumen and/or inflation of the inflatable lumen through introduction of a fluid into the inflatable lumen to change a volume of the feeding lumen, and the change in the volume allows for a change in pressure in the feeding lumen that affects a blockage of the enteral feeding device and allow for flow or delivery of medicaments, nutrients and/or fluids to a patient and the inflatable lumen is sized such that when full inflated a volume of the feeding lumen in the feeding tube allows for adequate flow of fluid and/or medicament and/or nutrient to a patient.

* * * * *